United States Patent [19]

Kucera

[11] 4,293,545
[45] Oct. 6, 1981

[54] MODIFIED *PASTEURELLA MULTOCIDA* BACTERIA VACCINES

[75] Inventor: Carrell J. Kucera, Lincoln, Nebr.

[73] Assignee: Norden Laboratories, Inc., Lincoln, Nebr.

[21] Appl. No.: 135,828

[22] Filed: Mar. 31, 1980

[51] Int. Cl.³ ............................................. A61K 39/02
[52] U.S. Cl. ..................................................... 424/92
[58] Field of Search ................................... 424/88–92, 424/93; 435/172

[56] References Cited

U.S. PATENT DOCUMENTS

| | | | |
|---|---|---|---|
| 3,501,770 | 3/1970 | Gale et al. | 424/89 |
| 3,526,696 | 9/1970 | Gale et al. | 424/89 |
| 3,634,587 | 1/1972 | Ament et al. | 424/89 |
| 3,855,408 | 12/1974 | Maheswaran | 424/92 |
| 4,167,560 | 9/1979 | Wohler | 424/92 |
| 4,169,886 | 10/1979 | Hertman | 424/92 |
| 4,171,354 | 10/1976 | Smith | 424/92 |

FOREIGN PATENT DOCUMENTS

| | | |
|---|---|---|
| 857014 | 3/1976 | Belgium . |
| 878430 | 12/1979 | Belgium . |
| 1030873 | 2/1974 | Canada . |
| 2816942 | 10/1978 | Fed. Rep. of Germany . |
| 7304320 | 10/1973 | Netherlands . |

OTHER PUBLICATIONS

Jensen et al., "Diseases of Feedlot Cattle", 3rd ed., Lea & Febiger, Philadelphia (1979), pp. 59–65.
Collins, "Mechanisms of Acquired Resistance to *Pasteurella multocida* Infection: A Review", Cornel Vet. 67(1):103 (1969).
Larson et al., J. Am. Vet. Med. Assn., 155:495 (1969).
Matsuoka et al., J. Am. Vet. Med. Assn., 160(3):333 (1972).
Sampson et al., Vet. Med. Small Anim. Clin., 67(12):1354 (1972).
Bierer et al., Poultry Science, 47(4):1258 (1968).
Rice et al., Poultry Science, 55(4):1605 (1976).
Carter et al., Am. J. Vet. Res., 39(9):1534 (1978).
Carter et al., Am. J. Vet. Res., 40(3):449 (1979).
Chengappa et al., Avian Disease, 23(1):57 (1979).
Brown et al., Appl. Microbiol., 19(5):837 (1970).
Rebers et al., Am. J. Vet. Res., 35(4):555 (1974).
Ganfield et al., Infect. Immun., 14(4):990 (1976).
Borisenkova et al., Veterinariya (Mosc.), 5:40 (1977).
Srivastava et al., Can. J. Microbiol., 23(2):197 (1977).
Baba, Infect. Immun., 15(1):1 (1977).
Nagy et al., Res. Vet. Sci., 20(3):249 (1976).
Mukkur, Infect. Immun., 18(3):583 (1977).
Gaunt et al., Avian Disease, 21(4):543 (1977).
Mukkur, Am. J. Vet. Res., 39(8):1269 (1978).

*Primary Examiner*—Delbert R. Phillips
*Assistant Examiner*—Blondel Hazel
*Attorney, Agent, or Firm*—Janice E. Williams; Richard D. Foggio; Alan D. Lourie

[57] ABSTRACT

The chemical modification of virulent *Pasteurella multocida* and *Pasteurella haemolytica* strains and preparation of live bacteria vaccines from the modified organisms for immunization of bovine, porcine and ovine animal species are disclosed.

12 Claims, No Drawings

MODIFIED *PASTEURELLA MULTOCIDA* BACTERIA VACCINES

This invention relates to Pasteurella bacteria and the preparation of vaccines therefrom. In particular, the invention relates to the modification of virulent *Pasteurella multocida* and *Pasteurella haemolytica* strains, to the preparation of mono- and polyvalent live bacteria vaccines from the modified organisms and to processes for preparing and using such vaccines.

*Pasteurella multocida* and *Pasteurella haemolytica* are known to infect bovine, porcine and ovine animal species causing respiratory disease, and have been implicated in the etiology of "shipping fever" syndrome. [Jensen et al., "Diseases of Feedlot Cattle", 3rd ed., Lea & Febiger, Philadelphia (1979), pgs. 59–65]. At present, pasteurellosis of domestic animals is controlled, with varying degrees of success, by the administration of vaccines, antimicrobial agents or a combination of the two.

Known vaccines for pasteurellosis contain killed whole cells (bacterins), live attenuated bacteria or cell fractions, with or without an adjuvant. One problem with the testing and use of such vaccines is that the highly variable cross-protection among *Pasteurella multocida* serotypes often results in the vaccine strain employed conferring little or no immunity against an infecting organism encountered under field conditions [Collins, "Mechanisms of acquired resistance to *Pasteurella multocida* infection: A review.", Cornell Vet. 67(1):103 (1977)].

Commercial bacterins, which usually contain one or more strains of formalin-killed Pasteurella, are undesirable due to several factors. At least two doses of such a vaccine, given several days apart, are necessary for effective protection (Collins, supra); they are often not successful and have been noted to cause transient endotoxic shock [Larson et al., J. Am. Vet. Med. Assn. 155:495 (1969)].

A number of combination vaccines containing killed Pasteurella are also known and used. For example, killed Pasteurella has been combined for use in cattle with bovine infections rhinotracheitis virus [Matsuoka et al., J. Am. Vet. Med. Assn. 160(3):333 (1972)]; with bovine parainfluenze-3 virus [Sampson et al., Vet. Med. Small Anim. Clin. 67(12):1354 (1972); U.S. Pat. No. 3,501,770 and U.S. Pat. No. 3,526,696]; in quadrivalent form, with bovine infectious rhinotracheitis virus, bovine viral diarrhea mucosal disease virus and bovine parainfluenze-3 virus (U.S. Pat. No. 3,634,587); and with *Salmonella typhimurium* (U.S. Pat. No. 4,167,560). German Offenlegungsschrift 2,816,942 discloses a cellular vaccine for atrophic rhinitis in pigs comprising killed *Pasteurella multocida* and *Bordetella bronchiseptica*. Avian vaccines, particularly for use against fowl cholera, containing killed Pasteurella alone or in combination with other bacteria or viruses are also known.

Avian and bovine vaccines containing live Pasteurella have also been developed. A turkey vaccine containing live attenuated *Pasteurella multocida* is described by Bierer et al., Poultry Science 47(4):1258 (1968), and in U.S. Pat. No. 3,855,408. Rice et al., Poultry Science 55(4):1605 (1976), describe the vaccination of chickens with a live *Pasteurella multocida* vaccine and U.S. Pat. No. 4,169,886 discloses a live fowl cholera vaccine prepared from the M-3-G strain of *Pasteurella multocida*.

Recently, a bovine vaccine for shipping fever, administered by intradermal injection, comprising a field strain live culture of *Pasteurella haemolytica* in a brain-heart infusion broth was disclosed in U.S. Pat. No. 4,171,354. Carter et al., Am. J. Vet. Res. 39(9):1534 (1978) and 40(3):449 (1979), have developed a hemorrhagic septicemia vaccine using a live streptomycin-dependent mutant of *Pasteurella multocida* which is highly immunogenic in mice, rabbits and calves. This vaccine also protected turkeys against fowl cholera [Chengappa et al., Avian Disease 23(1):57 (1979)].

Immunization of turkeys, chickens and/or mice with various cell fractions of *Pasteurella multocida* has also bee achieved, for example with culture filtrate, cell walls and cytoplasm [Brown et al., Appl. Microbiol. 19(5):837 (1970)], free endotoxin [Rebers et al., Am. J. Vet. Res. 35(4):555 (1974) and Canadian Pat. No. 1,030,873], a protein-polysaccharide complex isolated from the bacteria [Ganfield et al., Infect. Immun. 14(4):990 (1976)], cell membrane [Borisenkova et al., Veterinariya (Mosc.) 5:40 (1977)], a glycoprotein extract of a culture filtrate [Srivastava et al., Can. J. Microbiol. 23(2):197 (1977)] and a ribosomal fraction [Baba, Infect. Immun. 15(1):1 (1977)]. Nagy et al., Res. Vet. Sci. 20(3):249 (1976), describe the protection of cattle against hemorrhagic septicemia caused by *Pasteurella multocida* type E organisms with a vaccine comprising an extract of Pasteurella capsular material in an aluminum hydroxide adjuvant (see also Netherlands Pat. No. 73 04 320).

Ribosomal vaccines prepared from various organisms, including *Pasteurella multocida* and *Pasteurella haemolytica*, are described in Belgian Pat. No. 857,014. A potassium thiocyanate extract of *Pasteurella haemolytica* serotype 1 was found to be immunogenic and to produce cross-immunity in mice against *Pasteurella multocida* type A [Mukkur, Infect. Immun. 18(3):583 (1977)]. Chickens and calves have been protected against heterologous challenge with a potassium thiocyanate extract of *Pasteurella multocida* serotype 3 [Gaunt et al., Avian Disease 21(4):543 (1977); Mukkur, Am. J. Vet. Res. 39(8):1269 (1978)].

Until the present work, chemical modification of Pasteurella bacteria and preparation of a safe and highly effective vaccine for protecting animals, especially economically important feed animals, against the ravages of "shipping fever" and other Pasteurella associated diseases are not believed to have been accomplished. The vaccines produced from the new modified Pasteurella organisms of this invention have also been found to be cross-protective against a variety of Pasteurella spp field isolates.

One aspect of the present invention consists of safe and effective vaccines for the protection of bovine, porcine and ovine species of animals against upper respiratory disease associated with Pasteurella infection, including that commonly known as "shipping fever". Modified live *Pasteurella multocida* and *Pasteurella haemolytica* monovalent vaccines have been prepared for administration by the subcutaneous, intranasal or, preferably, intramuscular route. For administration to bovine and porcine species, such vaccines preferably contain from about $1.0 \times 10^7$ to about $1.0 \times 10^{11}$ CFU (colony forming units) per dose of the modified live *Pasteurella multocida* or the modified live *Pasteurella haemolytica* organisms with a suitable carrier and/or stabilizer. For administration to ovine species, the vaccine preferably contains from about $1.0 \times 10^9$ to about $1.0 \times 10^{11}$ CFU/dose of the modified *Pasteurella multocida* organism or from about $1.0 \times 10^7$ to about $1.0 \times 10^{11}$ CFU/dose of the modified *Pasteurella haemolytica* organism. The vaccines are administered in one or two doses, preferably two, of from 2.0 ml to 5.0 ml each, depending on the species and size of the animal being vaccinated as well as the organism count.

A bivalent vaccine consisting of vaccinal amounts of the modified live *Pasteurella multocida* and modified live *Pasteurella haemolytica* described herein is also an object of this invention. For administration to bovine and porcine species, such vaccine contains from about $1.0 \times 10^7$ to about $1.0 \times 10^{11}$ CFU/dose of each of the modified live Pasteurella strains with a suitable carrier and/or stabilizer. For administration to ovine species, the vaccine contains from about $1.0 \times 10^9$ to about $1.0 \times 10^{11}$ CFU/dose of the modified live *Pasteurella multocida* organisms and from about $1.0 \times 10^7$ to about $1.0 \times 10^{11}$ CFU/dose of the modified live *Pasteurella haemolytica* organisms. Such vaccine may be administered by the subcutaneous, intranasal or, preferably, intramuscular route in one or two doses, preferably two, of from 2.0 ml to 5.0 ml each.

Another aspect of the present invention consists of the new modified *Pasteurella multocida* and *Pasteurella haemolytica* organisms. These were deposited with the American Type Culture Collection in Rockville, Md. on Mar. 5, 1980 and have been assigned accession numbers 31610 (modified *Pasteurella multocida*) and 31612 (modified *Pasteurella haemolytica*). The organisms will be freely available on request upon issuance of this application, or any foreign equivalent thereof, as a patent.

The Pasteurella bacteria used to prepare the vaccines of this invention were isolated from lung tissue of infected animals and identified by standard identification methods. Both isolates were shown to be virulent by inoculation into mice and hamsters. Propagation of the bacteria was carried out in a liquid medium consisting of tryptose broth supplemented with thiamine (Difco Laboratories, Detroit, Mich.). Tryptose agar with 5% sheep blood was employed as a medium to determine the colonial characteristics of each of the Pasteurella parent bacteria.

The parent Pasteurella strains are chemically modified with acridinium salts, such as 3,6-bis-dimethylamino acridinium chloride (acridine orange), 2,8(3,6)diamino-10-methyl acridinium chloride and 2,8(3,6)diamino acridinium chloride (acriflavine HCl), in concentrations of from about 0.1 $\mu$g/ml to about 150 $\mu$g/ml in a medium consisting of tryptose supplemented with thiamine broth. The organisms may be passaged up to about 40 times in acridinium salt-supplemented broth with from about 8 to about 26 passages being preferred for the *Pasteurella multocida* and from about 10 to about 30 passages being preferred for the *Pasteurella haemolytica*. Upon modification, the morphological characteristics of the bacteria change from smooth, glistening and mucoid colonies of 1.5-2.0 mm diameter after incubation at 37° for 18 hours to rough, dull and punctiform colonies of 0.5-1.0 mm diameter after incubation. The chemically modified bacteria may be further grown and passaged in any suitable growth media, for example in tryptose broth supplemented with thiamine or in the medium described herein.

The vaccines of this invention are prepared by standard, known to the art methods, for example by combining the bacteria with a suitable carrier and/or a stabilizer.

DETAILED DESCRIPTION OF THE INVENTION

Isolation, Propagation and Chemical Modification of the Pasteurella Multocida Vaccine Strain The virulent *Pasteurella multocida* used to prepare the modified live organism of this invention (ATCC No. 31609) was obtained from and identified by the University of Nebraska, Department of Veterinary Sciences and was originally isolated from lung tissue of a gnotobiotic calf infected with the bacteria. The calf had been inoculated by the intratracheal route with a suspension of a pool of lung tissues from two diseased calves which had previously been similarly inoculated with pulmonary materials obtained from samples presented for laboratory studies. Within 36 hours following inoculation, the calf manifested clinical symptoms of a bacterial pneumonia, viz. elevated temperature, depression, cough and labored breathing. The animal was euthanized and, at necropsy, severe pneumonia with a fibrinous pleuritis was noted. Samples of the lung tissues were obtained aseptically and frozen at $-50°$ C.

Samples of the frozen tissues were thawed and streaked on blood agar plates. Selected colonies of the growth were identified by standard biochemical reactions as being typical of *Pasteurella multocida*. Other selected colonies were inoculated into a medium of tryptose broth supplemented with thiamine. Growth of the organisms was allowed to proceed at 37° C. for 16 hours. Aliquotes of the culture were then dispersed into small sterile vials which were stoppered with sterile neoprene stoppers, sealed and stored at $-70°$ C.

A vial of the frozen broth culture was thawed and inoculated into a 100 ml broth culture of tryptose broth supplemented with thiamine. Following incubation at 37° C. for 21 hours, a 1.0 ml volume of the culture was inoculated by the intracardiac route into a young adult New Zealand white rabbit. The inoculum contained about $2.0 \times 10^7$ CFU/ml. The rabbit was sacrificed eight hours after inoculation. Samples of liver and spleen and a quantity of blood were obtained. The tissues were homogenized, combined with the blood and frozen at $-70°$ C.

A vial of the frozen rabbit tissue containing the *Pasteurella multocida* organisms was thawed and two passages of the virulent organism were made in tryptose broth supplemented with thiamine. A small amount of the second passage material was inoculated into tryptose broth supplemented with acriflavine HCl at a level of 0.75 $\mu$g/ml. Following incubation for 24 hours at 37° C., a small amount of the bacterial growth was inoculated into tryptose broth containing 1.5 $\mu$g/ml of acriflavine HCl. Additional passages were made in tryptose broth supplemented with 1.5 $\mu$g/ml of acriflavine HCl.

Each passage of the organism in the presence of acriflavine HCl was monitored by streaking out the growth on the surface of blood agar plates to observe the purity of the culture and any changes in the morphology of the organism culture.

A change in the morphology of the colonies of the modified *Pasteurella multocida* strain was noted after a total of eight passages in the presence of acriflavine HCl. The parent organism and the organisms of the early passages in the presence of acriflavine HCl were smooth, glistening and mucoid. The size of these colonies following incubation at 37° C. for 18 hours was from 1.5 to 2.0 mm in diameter. The colonies of the eighth passage organisms streaked out on blood agar plates were rough and punctate. The size of the colonies was between 0.5 to 1.0 mm following incubation at 37° C. for 18 hours.

The chemically modified *Pasteurella multocida* strain was further passaged in acriflavine HCl supplemented broth and tested for purity and animal (hamster and mouse) $LD_{50}$ values following the 8th, 15th, 20th, 26th and 30th passages. The test animals were administered 0.1 ml of the vaccinal strain containing approximately $1.0 \times 10^{6-8}$ CFU by the intraperitoneal route. Following vaccination, the animals were challenged with known-virulent strains of *Pasteurella multocida*. The challenge strains employed were the Carter B (bison) strain, USDA strain #169 and USDA strain #1062 or isolates of *Pasteurella multocida* obtained from various university diagnostic laboratories. The challenge organisms generally had relatively low $LD_{50}$ values of from 1 to 100 organisms.

Those animals which had previously been vaccinated with one or two doses of the chemically modified strain from the 8th to the 26th passage levels resisted challenges of from one to greater than $1.0 \times 10^7$ virulent organisms. At the 26th passage level, the vaccine strain protected all of the vaccinated animals.

A single small colony of the modified *Pasteurella multocida* organism, 26th passage, was isolated and inoculated into tryptose broth supplemented with thiamine. Following incubation at 37° C. for 18 hours, a stabilizer was added to the growth medium as a freezing menstrum. The organism was dispensed in a number of vials which were frozen at −70° C. This lyophillized organism was deposited with the American Type Culture Collection in Rockville, Md. on Mar. 5, 1980 and has been assigned accession number 31610.

To determine the genetic stability of the modified *Pasteurella multocida* of this invention (ATCC No. 31610), the 26th passage material was passaged an additional 15 times in tryptose broth supplemented with thiamine. At the 5th, 10th and 15th passage levels in the absence of acriflavine, morphology of the colonies on blood agar plates was similar to that following exposure to 26 passages in acriflavine-containing medium. The protective properties of the 5th, 10th and 15th passages in acriflavine-free broth material remained unchanged. Virulence of the organisms after the 5th, 10th and 15th passages in acriflavine-free broth remained low and was equal to or greater than $1.0 \times 10^7$ organisms.

Preparation and Use of the Modified Live Pasteurella Multocida Vaccine

For vaccine preparation, the modified *Pasteurella multocida* strain (26th passage material) is further propagated in a suitable growth medium. An example of such suitable medium follows:

| Ingredient | Grams/Liter of Water |
|---|---|
| Bacto-Peptone | 10.0–40.0 |
| HY-Case Amino | 5.0–20.0 |
| NZ-Amine A | 5.0–20.0 |
| NZ-Amine B | 5.0–20.0 |
| Bacto-Yeast Extract | 5.0–20.0 |
| Sodium Chloride | 0.5–3.0 |

The above ingredients are combined and sterilized by autoclaving. A solution of 20.0–80.0 grams/liter of sucrose is separately sterilized by autoclaving and added to the other ingredients when cooled. The pH is adjusted to 7.4–7.6 with 10 N sodium hydroxide solution.

From one to four parts of growth medium containing the modified organisms are combined with one part of a stabilizer and lyophilized. An example of a suitable stabilizer follows:

| Solution 1 | |
|---|---|
| Ingredients | Grams/Liter of Water |
| Potassium Hydroxide (anhydrous) | 0.2–0.8 |
| L-glutamic acid | 0.5–2.0 |
| Potassium phosphate dibasic (anhydrous) | 1.0–4.0 |
| Potassium phosphate monobasic (anhydrous) | 0.3–1.5 |
| Sucrose | 50–200 |

The ingredients are combined and sterilized by autoclaving.

| Solution 2 | |
|---|---|
| Ingredients | Grams/Liter of Water |
| Gelatin (Knox) | 100–300 |
| Autoclave for four hours to hydrolyze. | |

Two parts of Solution 2 are added to three parts of Solution 1 to prepare the stabilizer solution.

Vaccination of Calves

The modified live *Pasteurella multocida* vaccine of this invention was administered in two 5.0 ml doses given by the subcutaneous or intramuscular routes at two week intervals to ten calves found to be devoid of protective antibodies. Nine of the calves were conventional dairy calves which had been deprived of colostrum after birth and one was a gnotobiotic animal obtained by cesarean section and maintained in an isolation unit. Two weeks following administration of the second dose of vaccine, all of the calves were challenged by intratracheal administration of *Pasteurella multocida* Carter type B organisms of demonstrated virulence when administered to calves by the subcutaneous and intratracheal routes. The results of this test appear in Table 1.

TABLE I

Protection Afforded Calves by Vaccination with a Modified Live Vaccine Prepared from ATCC No. 31610 Against a *Pasteurella Multocida* Carter type B Challenge

| Animal | Vaccination (CFU/5.0 ml) | | Route | Status Post-Challenge |
|---|---|---|---|---|
| | First Dose | Second Dose | | |
| 1* | $2.5 \times 10^9$ | $4.5 \times 10^8$ | Subcutaneous | Dead (120 hrs. P.C.)** |
| 2 | $3.4 \times 10^9$ | $5.5 \times 10^8$ | Subcutaneous | Normal |
| 3 | $3.4 \times 10^9$ | $5.5 \times 10^8$ | Subcutaneous | Normal |
| 4 | $3.4 \times 10^9$ | $5.5 \times 10^8$ | Subcutaneous | Normal |
| 5 | $3.4 \times 10^9$ | $5.5 \times 10^8$ | Subcutaneous | Normal |
| 6 | $3.4 \times 10^9$ | $5.5 \times 10^8$ | Intramuscular | Normal |
| 7 | $3.4 \times 10^9$ | $5.5 \times 10^8$ | Intramuscular | Normal |
| 8 | $3.4 \times 10^9$ | $5.5 \times 10^8$ | Intramuscular | Normal |
| 9 | $3.4 \times 10^9$ | $5.5 \times 10^8$ | Intramuscular | Normal |
| 10 | $3.4 \times 10^9$ | $5.5 \times 10^8$ | Intramuscular | Normal |
| A+ | — | — | — | Dead (48 hrs. P.C.) |
| B+ | — | — | — | moribund, |

TABLE I-continued

Protection Afforded Calves by Vaccination with a Modified Live Vaccine Prepared from ATCC No. 31610 Against a Pasteurella Multocida Carter type B Challenge

| Animal | Vaccination (CFU/5.0 ml) First Dose | Second Dose | Route | Status Post-Challenge |
|---|---|---|---|---|
| | | | | sacrificed |

*Gnotobiotic
**no Pasteurella found at necropsy
+Control

Vaccination of Swine

The modified live *Pasteurella multocida* vaccine of this invention was administered to four normal feeder weight pigs of from about 30–50 pounds each which were determined to be free of protective antibodies to *Pasteurella multocida* USDA strain #169. The animals were vaccinated with two 5.0 ml doses administered intramuscularly for 20 days apart. Two weeks following the administration of the second dose of the vaccine, the vaccinated animals and five non-vaccinated, serologically negative control animals were challenged by intravenous inoculation of $1.5 \times 10^9$ organisms of *Pasteurella multocida* USDA strain #169 contained in a 5.0 ml volume.

The vaccinated and control animals were maintained in separate clean rooms in an isolation building following challenge and were observed at least twice daily for 14 days. About three hours following the administration of the challenge material, the control animals showed signs of depression and respiratory distress. All of the control animals became uncoordinated and at about eight hours following the challenge they were recumbent. Two of the control animals died of an acute pneumonia at 40 and 58 hours following challenge. The remaining three control animals showed signs of respiratory difficulties and were appreciably depressed for several days. One of the control animals returned to a normal condition by the end of the observation period while the other two control animals remained depressed and failed to recover fully from the effects of the challenge.

The vaccinated animals were depressed and off feed for the first 8 to 12 hours following challenge, but returned to a normal state within 24 hours.

The results of this test appear in Table II.

TABLE II

Protection Afforded Swine by Vaccination with a Modified Live Vaccine Prepared from ATCC No. 31610 Against a Pasteurella Multocida USDA Strain #169 Challenge

| Animal | Vaccination (CFU/5.0 ml) First Dose | Second Dose | Status Post-Challenge | Comments |
|---|---|---|---|---|
| 1 | $9.0 \times 10^9$ | $1 \times 10^{10}$ | Alive and Well | Normal |
| 2 | $9.0 \times 10^9$ | $1 \times 10^{10}$ | Alive and Well | Normal |
| 3 | $9.0 \times 10^9$ | $1 \times 10^{10}$ | Alive and Well | Normal |
| 4 | $9.0 \times 10^9$ | $1 \times 10^{10}$ | Alive and Well | Normal |
| A* | — | — | Poor doing | Unthrifty |
| B* | — | — | Poor doing | Returned to Normal |
| C* | — | — | Died (58 hrs P.C.) | |
| D* | — | — | Poor doing | Unthrifty |
| E* | — | — | Died (40 hrs P.C.) | |

*Control

Vaccination of Sheep

The modified live *Pasteurella multocida* vaccine of this invention was administered to ten unvaccinated susceptible sheep ranging in weight from 40 to 130 pounds which were obtained from a flock having a history of being free of respiratory disease problems. The animals were divided into two groups which were vaccinated with two different levels of the vaccine. One group of animals received vaccine containing about $1.0 \times 10^{10}$ CFU/5.0 ml dose and the other group was vaccinated with approximately $4.0 \times 10^8$ CFU/5.0 ml dose. The interval of time between the administration of the two doses of the vaccine was 20 days.

Fourteen days following the second vaccination the vaccinated sheep and a control group were challenged by intravenous administration of approximately $3.0 \times 10^9$ CFU/3.0 ml volume of *Pasteurella multocida* USDA strain #1062. Following challenge, the animals were observed at least twice a day for a period of 14 days.

It was noted that within four hours after challenge the control animals became depressed and exhibited signs of respiratory distress. Within several hours the animals of this group became increasingly more depressed and breathing became labored. Two of the control animals died of pneumonia, one at 38 hours following challenge and one at 148 hours. The surviving three animals remained depressed and were recumbent for prolonged periods. Each of the control animals developed joint swellings and exhibited depression and varying degrees of locomotion and breathing difficulty.

The five sheep vaccinated with two reduced doses of the vaccine showed essentially the same signs and symptoms following challenge as did the control animals. Three of these animals died at 65, 73 and 294 hours following challenge. Extensive pneumonia was observed in each of these animals at necropsy. The two surviving animals failed to return to a normal status and were weak and depressed throughout the post-challenge period.

The animals vaccinated with two doses of vaccine containing $1.0 \times 10^{10}$ CFU/dose were slightly depressed and went off feed immediately following challenge. Within 24 hours after challenge the animals, with the exception of one animal which developed a limp, returned to normal. During the remainder of the observation period, the animals of this group exhibited transient lameness and periodically showed some depression. One animal became depressed and quite lame near the end of the observation period and was sacrificed at termination of the test. At necrospy a small area of pneumonia was observed in one lobe and *Pasteurella multocida*-like organisms were recovered from the involved joint fluids.

Table III presents the results of this test.

TABLE III

Protection Afforded Sheep by Vaccination with a Modified Live Vaccine Prepared from ATCC No. 31610 Against a Pasteurella Multocida Strain #1062 Challenge

| Animal | Vaccination (CFU/5.0 ml) First Dose | Second Dose | Status Post-Challenge | Comments |
|---|---|---|---|---|
| 1 | $9.0 \times 10^9$ | $1.0 \times 10^{10}$ | Alive | Normal |
| 2 | $9.0 \times 10^9$ | $1.0 \times 10^{10}$ | Alive | Normal |
| 3 | $9.0 \times 10^9$ | $1.0 \times 10^{10}$ | Alive | Normal |
| 4 | $9.0 \times 10^9$ | $1.0 \times 10^{10}$ | Alive | Depressed, |

TABLE III-continued

Protection Afforded Sheep by Vaccination with a Modified Live Vaccine Prepared from ATCC No. 31610 Against a *Pasteurella Multocida* Strain #1062 Challenge

| Animal | Vaccination (CFU/5.0 ml) First Dose | Second Dose | Status Post-Challenge | Comments |
|---|---|---|---|---|
| 5 | $9.0 \times 10^9$ | $1.0 \times 10^{10}$ | Alive | Lameness, Sacrificed Normal |
| 6 | $3.6 \times 10^8$ | $4.0 \times 10^8$ | Poor doing | Sacrificed |
| 7 | $3.6 \times 10^8$ | $4.0 \times 10^8$ | Poor doing | Died (32 days P.C.) |
| 8 | $3.6 \times 10^8$ | $4.0 \times 10^8$ | Died (254 hrs P.C.) | |
| 9 | $3.6 \times 10^8$ | $4.0 \times 10^8$ | Died (73 hrs P.C.) | |
| 10 | $3.6 \times 10^8$ | $4.0 \times 10^8$ | Died (65 hrs P.C.) | |
| A* | — | — | Poor doing | Depressed, Joint Problems |
| B* | — | — | Poor doing | Depressed, Joint Problems |
| C* | — | — | Poor doing | Died (25 days P.C.) |
| D* | — | — | Died (38 hrs P.C.) | |
| E* | — | — | Died (148 hrs P.C.) | |

*Control

Isolation, Propagation and Chemical Modification of the Pasteurella Haemolytica Vaccine Strain The parent *Pasteurella haemolytica* used to prepare the modified live organism of this invention (ATCC No. 31611) was isolated from lung tissue aseptically removed from a calf, submitted to the University of Nebraska, Department of Veterinary Sciences, which had died from "shipping fever" and frozen at $-50°$ C.

Samples of the frozen tissues were thawed and streaked on the surfaces of sheep blood agar plates. Following incubation at 37° C. for 24 hours, a pure culture of colonies resembling Pasteurella spp was observed. Several colonies were selected and inoculated into test media for identification. The results of the tests indicated the organism to be *Pasteurella haemolytica*.

Other colonies of the organism were inoculated into a medium of tryptose broth supplemented with thiamine. Following incubation at 37° C. for 24 hours, an additional passage was made in the same medium. A volume of a stabilizer solution, described above, was added to the growth of the organism. The growth-stabilizer mixture was dispensed in 2.0 ml aliquots and subjected to lyophilization. The lyophilized parent organism was stored at 4° C. Colonies of the parent organism following incubation at 37° C. for 24 hours were circular, glistening and mucoid. The colonies were about 2.0 mm in diameter.

A lyophilized sample of the parent organism was rehydrated, inoculated into a medium of tryptose broth supplemented with 1.5 $\mu$g of acriflavine HCl/ml and was subjected to three passages in this broth. In subsequent passages, the concentration of acriflavine HCl was increased. In the 6th passage, the concentration of acriflavine HCl was 15.0 $\mu$g/ml. In the 10th passage, the colonies of the organism were punctiform, dull and rough with a diameter of about 0.5 mm.

Concomitant with the changes in the size and characteristics of the colonies of the acriflavine-treated organisms, a marked reduction in the virulence of the modified organisms was noted. The $LD_{50}$ values in mice for the parent and chemically modified strains were $2.9 \times 10^3$ and $7.3 \times 10^6$ CFU, respectively. In hamsters, the $LD_{50}$ values for the parent organism and for the chemically modified strain were $1.1 \times 10^6$ and $\geq 6.2 \times 10^8$ CFU, respectively.

Following 12 passages in acriflavine HCl-supplemented medium, the modified organism was passaged 15 times in a medium not supplemented with acriflavine HCl. The 15th passage level material produced $LD_{50}$ values in mice and hamsters nearly identical to that produced by material prior to passage in acriflavine-free medium.

Preparation and Use of the Modified Live Pasteurella Haemolytica Vaccine

For preparation of a vaccine, further quantities of the modified *Pasteurella haemolytica* (12th passage) are grown in a suitable medium, such as that described above for propagation of the modified *Pasteurella multocida*, combined with a stabilizer and lyophilized. An example of a stabilizer which may be employed is described above.

A further aspect of this invention is the preparation and use of a combination vaccine consisting of vaccinal amounts of the modified live *Pasteurella multocida* and the modified live *Pasteurella haemolytica* bacteria. Such combination vaccine will, preferably, contain from about $1.0 \times 10^7$ to about $1.0 \times 10^{11}$ CFU/dose of each of the modified live Pasteurella strains for vaccination of bovine and porcine species or from about $1.0 \times 10^9$ to about $1.0 \times 11^{11}$ CFU/dose of the modified live *Pasteurella multocida* strain and from about $1.0 \times 10^7$ to about $1.0 \times 10^{11}$ CFU/dose of the modified live *Pasteurella haemolytica* strain for vaccination of ovines. The vaccine can be prepared for subcutaneous, intramuscular or intranasal administration and is administered in one or two doses of from 2.0 ml to 5.0 ml each.

The preparation and use of such combination vaccines is carried out according to procedures described herein or within the knowledge of those skilled in the art of vaccine production and use.

What is claimed is:

1. A modified live *Pasteurella multocida* vaccine capable of inducing immunity in bovine, porcine and ovine animal species without serious side effects comprising a vaccinal amount of modified live *Pasteurella multocida* bacteria prepared by chemical modification of virulent *Pasteurella multocida* strain ATCC No. 31609 with an acridinium salt, and a carrier therefor.

2. The modified live *Pasteurella multocida* vaccine of claim 1 wherein the virulent organism is passaged from about one to about 40 times in the presence of an acridinium salt.

3. The modified live *Pasteurella multocida* vaccine of claim 2 wherein the virulent organism is passaged from about 8 to about 26 times in the presence of an acridinium salt.

4. The modified live *Pasteurella multocida* vaccine of claim 3 wherein the acridinium salt is acriflavine HCl.

5. The modified live *Pasteurella multocida* vaccine of claim 4 wherein the virulent organism is passaged 26 times.

6. The modified live *Pasteurella multocida* vaccine of claim 5 wherein the modified *Pasteurella multocida* bacteria is ATCC No. 31610.

7. The modified live *Pasteurella multocida* vaccine of claim 6 for administration to bovine and porcine animal species comprising from about $1.0 \times 10^7$ to about $1.0 \times 10^{11}$ CFU/dose of the modified bacteria.

8. The modified live *Pasteurella multocida* vaccine of claim 6 for administration to bovine, porcine and ovine animal species comprising from about $1.0 \times 10^9$ to about $1.0 \times 10^{11}$ CFU/dose of the modified bacteria.

9. A method of vaccinating bovine, porcine and ovine animal species comprising administering to said animals the modified live *Pasteurella multocida* vaccine of claim 1.

10. A method of vaccinating bovine and porcine animal species comprising administering to said animals the modified live *Pasteurella multocida* vaccine of claim 7.

11. A method of vaccinating bovine, porcine and ovine animal species comprising administering to said animals the modified live *Pasteurella multocida* vaccine of claim 8.

12. The method of claim 9, 10 or 11 wherein the modified live *Pasteurella multocida* vaccine is administered subcutaneously, intranasally or intramuscularly.

* * * * *